United States Patent [19]

Saul et al.

[11] Patent Number: 5,573,943
[45] Date of Patent: Nov. 12, 1996

[54] CLONING AND EXPRESSION OF A RHOPTRY ASSOCIATED PROTEIN OF P. FALCIPARUM

[75] Inventors: Allan J. Saul, The Gap; Juän A. Cooper, Alderly; David O. Irving, Lane Cove, all of Australia

[73] Assignee: Saramane Pty. Ltd., Victoria, Australia

[21] Appl. No.: 971,759

[22] PCT Filed: Aug. 1, 1991

[86] PCT No.: PCT/AU91/00338

§ 371 Date: Apr. 1, 1993

§ 102(e) Date: Apr. 1, 1993

[87] PCT Pub. No.: WO92/02623

PCT Pub. Date: Feb. 20, 1992

[30] Foreign Application Priority Data

Aug. 2, 1990 [AU] Australia .............................. PK1525/90

[51] Int. Cl.⁶ .............................. C12N 1/21; C07H 21/04; C07K 14/445
[52] U.S. Cl. ...................... 435/252.3; 424/268.1; 424/272.1; 435/69.3; 435/252.8; 435/320.1; 530/350; 530/395; 530/806; 536/23.5
[58] Field of Search .................... 424/88, 184.1, 424/185.1, 268.1, 272.1; 514/2.8; 530/350, 395, 806; 435/69.3, 252.3, 252.8, 320.1; 530/350, 395, 806

[56] References Cited

PUBLICATIONS

Perrin, L. H. et al., J. Clin. Invest. 75:1718–1721 (May, 1985), "Immunization with a Plasmodium falciparum merozoite surface antigen induces a partial immunity in monkeys".

Bushell, G. R., et al., Mol. Biocehm. Parasitol. 28:105–112 (1988), "an antigenic complex in the rhoptries of *Plasmodium falciparum*".

Clark, J. T., et al., Parasitol. Res. 73(5): 425–434 (1987), "Identification and charaterisation of proteins associated with the rhoptry organelles of *Plasmodium falciparum* merozoites".

Coppel, R. L., et al., Mol. Biochem. Parasitol. 25:73–81 (1987), "A cDNA clone expressing a rhoptry protein of *P. falciprum*".

Cox, F. E. G., Tibtech 9:389–394 (Nov., 1991), "Malaria vaccines–progress and problems".

*Primary Examiner*—Thomas M. Cunningham
*Attorney, Agent, or Firm*—Sughrue, Mion, Zinn, Macpeak & Seas

[57] ABSTRACT

A synthetic or recombinant polypeptide displaying the antigenicity of the 42 kDa rhoptry-associated protein (RAP-2) of *P.falciparum* or an antigenic fragment thereof, and recombinant DNA molecules, vectors and host cells for the expression thereof.

8 Claims, 10 Drawing Sheets

FIG. 3A

```
 -79        ATATATATA TATATATATA AAAAAAAA GAGCAACAAA
 -40   TTTGTTTTTA TTTTTAATAT AACATCATAC AGTTAAAAAA

1   ATG GGT TTA AAA TTT TAT GTA TTA GTT TTT CTT
   1   Met Gly Leu Lys Phe Tyr Val Leu Val Phe Leu

34   GGG GAT AAG TGT GAA ACT GAA TTT TCA AAA TTA
  12   Gly Asp Lys Cys Glu Thr Glu Phe Ser Lys Leu

67   TTA ATT TAT GCA CAC ACT GCA CAT GTT CAT AAA
  23   Leu Ile Tyr Ala His Thr Ala His Val His Lys

100   AAT CAC TTT AGT GCA AGT GAT GAA GTT TTA AAA
  34   Asn His Phe Ser Ala Ser Asp Glu Val Leu Lys

133   TTA GAA AAT CAC GAT AGT CAT ACA TGT TTT AGA
  45   Leu Glu Asn His Asp Ser His Thr Cys Phe Arg

166   TAT CTT AAG GAT ATT AAG TCT ATG TTA TTA GCT
  56   Tyr Leu Lys Asp Ile Lys Ser Met Leu Leu Ala

199   AAA TTC AAA GAT ATT AAT CCA GAT TTG TTT AGT
  67   Lys Phe Lys Asp Ile Asn Pro Asp Leu Phe Ser

232   AAA TTT ATG AAG GAA AAT CTG TTT TTA TAT ATT
  78   Lys Phe Met Lys Glu Asn Leu Phe Leu Tyr Ile

265   ATA AAG TAC TAT AAT CCA TAC TTT CGT ATA ATA
  89   Ile Lys Tyr Tyr Asn Pro Tyr Phe Arg Ile Met

298   TAT AAG TAT CGA TAC TTT TTA ATA GTA GGA TCA
 100   Tyr Lys Tyr Arg Tyr Phe Leu Ile Val Gly Ser

331   TTT GGA GAT TTT AAT AAA TAT ACT GAG ATA AGT
 111   Phe Gly Asp Phe Asn Lys Tyr Thr Glu Ile Ser
```

FIG. 3B

| | | | | | | | | |
|---|---|---|---|---|---|---|---|---|
| 364 122 | ATT Ile | TTA Leu | TGT Cys | TTG Leu | AAG Lys | AAT Asn | GTT Val | GTA Val | AAA Lys |
| 391 131 | TAT Tyr | CCG Pro | GAA Glu | TCA Ser | AAT Asn | TCT Ser | TTG Leu | ACT Thr | GGT Gly |
| 418 140 | TTA Leu | TCT Ser | ATG Met | TGG Trp | GTT Val | TAT Tyr | TTT Phe | ATT Ile | TAT Tyr |
| 445 149 | TAT Tyr | TTA Leu | GAA Glu | AAA Lys | ACC Thr | AAC Asn | ATA Ile | AAT Asn | ACT Thr |
| 472 158 | GCA Ala | GTT Val | ACT Thr | TTA Leu | TAT Tyr | TTG Leu | TTT Phe | TAT Tyr | TAC Tyr |
| 499 167 | GAT Asp | TAT Tyr | CAA Gln | TCA Ser | TTT Phe | TTT Phe | AAG Lys | AAT Asn |
| 526 176 | GAT Asp | TTT Phe | ATT Ile | TTA Leu | ATT Ile | CTT Leu | AAT Asn | GAT Asp | AAG Lys |
| 553 185 | AAA Lys | GAA Glu | TCT Ser | GAG Glu | AGA Arg | GAA Glu | CAT His | CAT His | TTG Leu |
| 580 194 | AAA Lys | GCA Ala | TCA Ser | ACT Thr | ACT Thr | ACA Thr | CAT His | CAT His | GCA Ala |
| 607 203 | AGA Arg | GTT Val | CAT His | ACA Thr | CCT Pro | TAT Tyr | AAA Lys | GAT Asp | GAT Asp |
| 634 212 | GTA Val | CTT Leu | AAT Asn | TAT Tyr | TAT Tyr | GTT Val | CGT Arg | GAT Asp | TAC Tyr | AAT Asn |

FIG. 3C

| | | | | | | | | | | |
|---|---|---|---|---|---|---|---|---|---|---|
| 661 | TTT | TTA | ATT | TAT | GCT | GGT | TCA | AGG | GAA | AAT | TAC |
| 221 | Phe | Leu | Ile | Tyr | Ala | Gly | Ser | Arg | Glu | Asn | Tyr |
| 694 | AGA | AGT | GTT | AAT | AAT | GTA | ATT | AGT | AAG | AAT | AAA |
| 232 | Arg | Ser | Val | Asn | Asn | Val | Ile | Ser | Lys | Asn | Lys |
| 727 | TCT | CTC | GCT | TTA | GTA | GGA | ACA | AAT | AAC | AAT | GAC |
| 243 | Ser | Leu | Ala | Leu | Val | Gly | Thr | Asn | Asn | Asn | Asp |
| 760 | AAT | TCA | GAA | TAT | TAC | GGT | ACA | CCA | GAT | GAT | GAT |
| 254 | Asn | Ser | Glu | Tyr | Tyr | Gly | Thr | Pro | Asp | Asp | Asp |
| 793 | AAA | ACT | AAA | ATG | TTA | AAT | TCT | CAT | AAA | ACG | TTT |
| 265 | Lys | Thr | Lys | Met | Leu | Asn | Ser | His | Lys | Thr | Phe |
| 826 | CAC | AAA | ACA | TAT | TCA | ATA | CCT | AAC | TTA | AAA | GGT |
| 276 | His | Lys | Thr | Tyr | Ser | Ile | Pro | Asn | Leu | Lys | Gly |
| 859 | AAA | AAG | AAT | TTA | GTG | AAT | TTT | GTA | GGT | ATG | TAT |
| 287 | Lys | Lys | Asn | Leu | Val | Asn | Phe | Val | Gly | Met | Tyr |
| 829 | TTC | TTA | GCT | GAT | TTA | GAT | TTC | GTT | GAA | TTA | TTT | GAT |
| 298 | Phe | Leu | Ala | Asp | Leu | Asp | Phe | Val | Glu | Leu | Phe | Asp |
| 925 | TAT | TCA | AAC | CGT | GCT | GCA | GAA | AAC | TTC | AAA | GCT |
| 309 | Tyr | Ser | Asn | Arg | Ala | Ala | Glu | Asn | Phe | Lys | Ala |
| 958 | TAC | AAT | TCA | GAT | ATA | GCT | GGA | CCA | GCA |
| 320 | Tyr | Asn | Ser | Asp | Ile | Ala | Gly | Pro | Ala |
| 985 | ACA | TTA | GGA | TTG | AGA | AAA | CGT | AGT | AGT |
| 329 | Thr | Leu | Gly | Leu | Arg | Lys | Arg | Ser | Ser |

FIG. 3D

| | | | | | | | | | |
|---|---|---|---|---|---|---|---|---|---|
|1012|CCT|ATA|TTT|GCT|TAT|TGT|GAA|AAA|GAT|
|338|Pro|Ile|Phe|Ala|Tyr|Cys|Glu|Lys|Asp|

| | | | | | | | | | |
|---|---|---|---|---|---|---|---|---|---|
|1039|TTA|ATT|ACA|TCT|TTC|TTT|TCA|ATT|ATA|
|347|Leu|Ile|Thr|Ser|Phe|Phe|Ser|Ile|Ile|

| | | | | | | | | | |
|---|---|---|---|---|---|---|---|---|---|
|1066|TTA|AGA|CAA|TTT|GAT|TAT|GCT|TTA|TTT|
|356|Leu|Arg|Gln|Phe|Asp|Tyr|Ala|Leu|Phe|

| | | | | | | | | | |
|---|---|---|---|---|---|---|---|---|---|
|1093|TTC|AGA|TTT|TTG|AAA|CAC|CTT|TTC|CAA|
|365|Phe|Arg|Phe|Leu|Lys|His|Leu|Phe|Gln|

| | | | | | | | | | |
|---|---|---|---|---|---|---|---|---|---|
|1120|GAA|AAT|CAC|GTA|TCA|ACA|GAA|ATA|AAT|
|374|Glu|Asn|His|Val|Ser|Thr|Glu|Ile|Asn|

| | | | | | | | | | |
|---|---|---|---|---|---|---|---|---|---|
|1147|GTA|ACT|ATG|GAT|TGT|TAT|TCT|CGC|CAA|
|383|Val|Thr|Met|Asp|Cys|Tyr|Ser|Arg|Gln|

| | | | | | | | | | |
|---|---|---|---|---|---|---|---|---|---|
|1174|ATT|AGA|GAA|TTA|AAT|GTT|CTT|TAA|AAT|
|392|Ile|Arg|Glu|Leu|Asn|Val|Leu|TER| |

1201 AAAATACATT TATAAATAAA CATATAACTA TTACAAAATA CACATTTTA TATTAAAGG
1261 TTTCTCATAA ATATGTTTT TATTTTAATT GTTTGCTTTT GTTTATTAA ACTTTTTGT
1321 TATTTTATTT TATTTTAATT TATTTTAAT TTTTTTTTT TTTGTTTTAA ATATTCTTT AAGTTGACAT
1381 TTAAATATTA TATTACAAGG AAAAGTCTT AAATATATAT ATATATAT GTATATATTT
1441 TCTTTTAATG GGTAAAAAG (SEQ ID NO: 19)

FIG. 3E

```
          DNA SEQUENCE
          130        140        150
D10  GCACACACTGCACACATGTTCATAAATTA   SEQ ID NO:20, WHEREIN M IS C
HB3  ..........A.................
307  ..........A.................   SEQ ID NO:20, WHEREIN M IS A
PA   ..........A.................
```

FIG. 3F

```
     PROTEIN SEQUENCE
            70
D10  AHTAHVHKL        SEQ ID NO:21, WHEREIN X_{aa} IS H
HB3  ....N....
307  ....N....        SEQ ID NO:21, WHEREIN X_{aa} IS N
PA   ....N....
```

```
       DNA SEQUENCE
       540        550        560        570        580        590        600
D10    TTATAAGTATAATCCATACTTTATAGTAGGATCAAGAGTTCATACACCTTATAAAGATTACTTTGGA  SEQ ID NO:22,
                                                                             WHEREIN M IS A,
                                                                             Y IS T, W IS T

HB3    ..........C.........................................C............  SEQ ID NO:22,
                                                                             WHEREIN M IS C,
                                                                             Y IS C, W IS T

3D7    ..........C...............................A......................  SEQ ID NO:22,
                                                                             WHEREIN M IS C,
                                                                             Y IS T, W IS A

PA     ..........C.........................................C............  SEQ ID NO:22,
                                                                             WHEREIN M IS C,
                                                                             Y IS C, W IS T
```

```
          PROTEIN SEQUENCE
          190        200
D10    YKYNRYFIVGSRVHTPYKDYFG    SEQ ID NO:23,    WHEREIN X_aa AT RESIDUE 3
                                                  IS Y & X_aa AT RESIDUE 21 IS
                                                  F
HB3    ..S.................L.
307    ..S.................L.   SEQ ID NO:23,    WHEREIN X_aa AT RESIDUE 3
                                                  IS S & X_aa AT RESIDUE 23 IS
                                                  L
PA     ..S.................L.
```

CLONING AND EXPRESSION OF A RHOPTRY ASSOCIATED PROTEIN OF P. FALCIPARUM

This invention relates to the cloning of the gene encoding a rhoptry associated protein of *Plasmodium falciparum*, to the recombinant polypeptide produced by expression of this gene in a host cell, and to the use of this recombinant polypeptide in a vaccine against the malaria parasite.

In many parts of the world, malaria is proving refractory to control measures aimed at the vector and the parasite. Advances in molecular biology have opened up the possibility of augmenting existing control programmes with vaccines directed against the parasite. Several stages in the life cycle of the parasite are under intense scrutiny as targets of such putative vaccines; these include the sporozoite coat protein, various proteins found in the asexual erythrocytic blood stages and proteins on the surface of the mosquito stages (Miller et.al., 1986).

The stage of the parasite which invades erythrocytes is the merozoite. At this stage, there are has a pair of organelles at the apical end of the parasite, the rhoptries, that are involved in the invasion process. During invasion the contents of the rhoptries are discharged through ducts and may play an initial role in the formation of the developing parasitophorous vacuole. Antigens in the rhoptry contents were amongst the first components identified as potential vaccine candidates. Freeman et.al. (1980) showed that a monoclonal antibody against a protein found in the rhoptries of the rodent malaria *Plasmodium yoelii* was able to confer passive protection in mice challenged by an otherwise lethal strain of *P. yoelii*. The target of this monoclonal antibody was purified and shown to induce active protection upon immunization (Holder and Freeman, 1981).

The rhoptries of the human malarial parasite *P.falciparum* have been intensively studied and many proteins have been found which are associated with the rhoptries or associated apical organelles. These include: a 225 kDa antigen (Roger et.al., 1988), a complex consisting of proteins of about 140, 130 and 105 kDa (Campbell et.al., 1984; Holder et.al., 1985; Siddiqui et.al., 1986; Cooper et.al., 1988), a complex consisting of an 80 and a 42 kDa protein (Perrin and Dayal, 1982; Campbell et.al., 1984; Howard et.al., 1984; Schofield et.al., 1986; Clark et.al., 1987; Bushell et.al., 1988), a phospholipase activated protease (Braun-Breton et.al., 1988) and individual proteins of about 80 kDa (Peterson et.al., 1989; Crewther et.al., 1990) and 55 kDa (Smythe et.al., 1988).

The reported sizes of the components of the 80/42 kDa complex (referred to as QF3 by Schofield et.al.(1986) and Bushell et.al., (1988)) have varied from 80 to 82 kDa and 40 to 42 kDa. In some studies, an 83 kDa, short-lived precursor of the 80 kDa; a series of breakdown products of the 80 kDa; and a 40 kDa derivative of the 42 kDa protein have been reported (Bushell et.al., 1988). In the following description, the complex will be referred to as QF3 but following the nomenclature of Ridley et.al. (1990a), the 80 kDa component will be referred to as RAP-1 (Rhoptry Associated Protein 1) and the 42 kDa component as RAP-2 (Rhoptry Associated Protein 2).

There are several published reports suggesting that the QF3 complex is a likely candidate for a vaccine against *P.falciparum*. Monoclonal antibodies directed against QF3 give marked inhibition of parasite growth in vitro (Schofield et.al., 1986). Ridley et.al., (1990b) found that a mixture of affinity purified RAP-1 and RAP-2 was able to immunize Saimiri monkeys. These monkeys developed antibodies against both RAP-1 and RAP-2 and showed substantial protection when challenged with *P.falciparum*. Perrin et.al., (1985) also obtained substantial protection in Saimiri monkeys following immunization with mixtures containing either 80 and 40 kDa rhoptry proteins or with mixtures of several 40 kDa rhoptry proteins. The interpretation of these results is complicated since the proteins were purified using a mixture of 3 monoclonal antibodies. These now appear to be directed against several different proteins including aldolase (Certa et.al., 1988), a rhoptry associated protease (Braun-Breton et.al., 1988) and QF3.

Recently, Ridley et.al., (1990a) have described the cloning of the 80 kDa RAP-1 protein. The present invention arises from the work directed to the cloning, and sequencing of the gene of the 42 kDa RAP-2 protein and investigation of the properties of recombinant RAP-2 expressed in host cells such as bacteria. From the data obtained in this work, it has been established that RAP-2 is not the *P.falciparum* aldolase (Certa et.al., 1988), not a serine protease (Braun-Breton et.al., 1988) nor related to RAP-1 (Perrin and Dayal, 1982; Ridley et.al., 1990a) as has been suggested. The protein shows a number of unusual characteristics for proteins identified as malarial antigens. It is a basic protein with no repetitive elements and shows minimal sequence diversity in a number of isolates.

According to the present invention, there is provided a recombinant DNA molecule comprising a nucleotide sequence which codes on expression for a polypeptide having the antigenicity of the 42 kDa rhoptry-associated protein (RAP-2) of *P.falciparum* or an antigenic fragment thereof. In particular, this invention provides a recombinant DNA molecule comprising a nucleotide sequence corresponding to all or a portion of the nucleotide sequence as set out in of FIG. 3A herein, or degenerate allelic variants thereof. Such a nucleotide sequence codes on expression for a polypeptide corresponding to all or an antigenic fragment of the amino acid sequence of FIG. 3A or allelic variants thereof. The recombinant DNA molecule may also comprise an expression control sequence operatively linked to the nucleotide sequence as described above.

The present invention also extends to a recombinant DNA cloning vector containing a recombinant DNA molecule as broadly described above, as well as to a host cell containing such a recombinant DNA molecule or recombinant DNA cloning vector.

Finally, this invention further extends to a synthetic or recombinant polypeptide displaying the antigenicity of all or a portion of the 42 kDa rhoptry-associated protein of *P.falciparum*, as well as to compositions for stimulating an immune response against the 42 kDa rhoptry-associated protein of *P.falciparum* which comprise the recombinant polypeptide as described above. The recombinant polypeptide is of course produced by expression in a host cell as described above.

BRIEF DESCRIPTION OF THE DRAWINGS

FIG. 2A shows gels stained with Coomassie blue.

FIG. 2B shows an immunoblot where the protein was transferred to nitrocellulose and probed with MAb 3A9/48 as previously described (Bushell et al., 1988). Position of the RAP-2 is indicated: on this 12% gel system, RAP-2 has an apparent size of 35 kDa, previous estimates of approximately 40 kDa were based on 7.5% polyacrylamide gels.

FIGS. 3A to 3D show the nucleotide sequence (SEQ ID NO:19) and the deduced amino acid sequence encoded by residues 61-1254 of SEQ ID NO:19 of the RAP-2 clone. Note that the SEQ ID numbering is different from that in the Figures.

FIGS. 3E to 3H show the polymorphism detected in the RAP-2 sequences of the D10, 3D7, HB3 and Palo Alto lines in the nucleotide (FIGS. 3E and 3G) and translated amino acid (FIGS. 3F and 3H) sequences.

FIG. 3E shows the nucleotide sequence denoted as SEQ ID NO:20 wherein M is C for D10 and wherein M is A for HB3, 3D7 and PA.

FIG. 3F shows the amino acid sequence denoted as SEQ ID NO:21 wherein Xaa is H for D10, and Xaa is N for HB3, 3D7 and PA.

FIG. 3G shows the nucleotide sequence denoted as SEQ ID NO:20 wherein M is A, Y is T, and W is T for D10; M is C, Y is C, and W is T for HB3; M is C, Y is T, and W is A for 3D7; and M is C, Y is C, and W is T for PA.

FIG. 3H shows the amino acid sequence denoted as SEQ ID NO:23 wherein Xaa at residue 3 is Y and Xaa at residue 21 is F for D10; and wherein Xaa at residue 3 is S and Xaa at residue 23 is L for HB3, and 3D7 and PA.

Note that the SEQ ID numbering is different from that in the figures.

Figure 4:
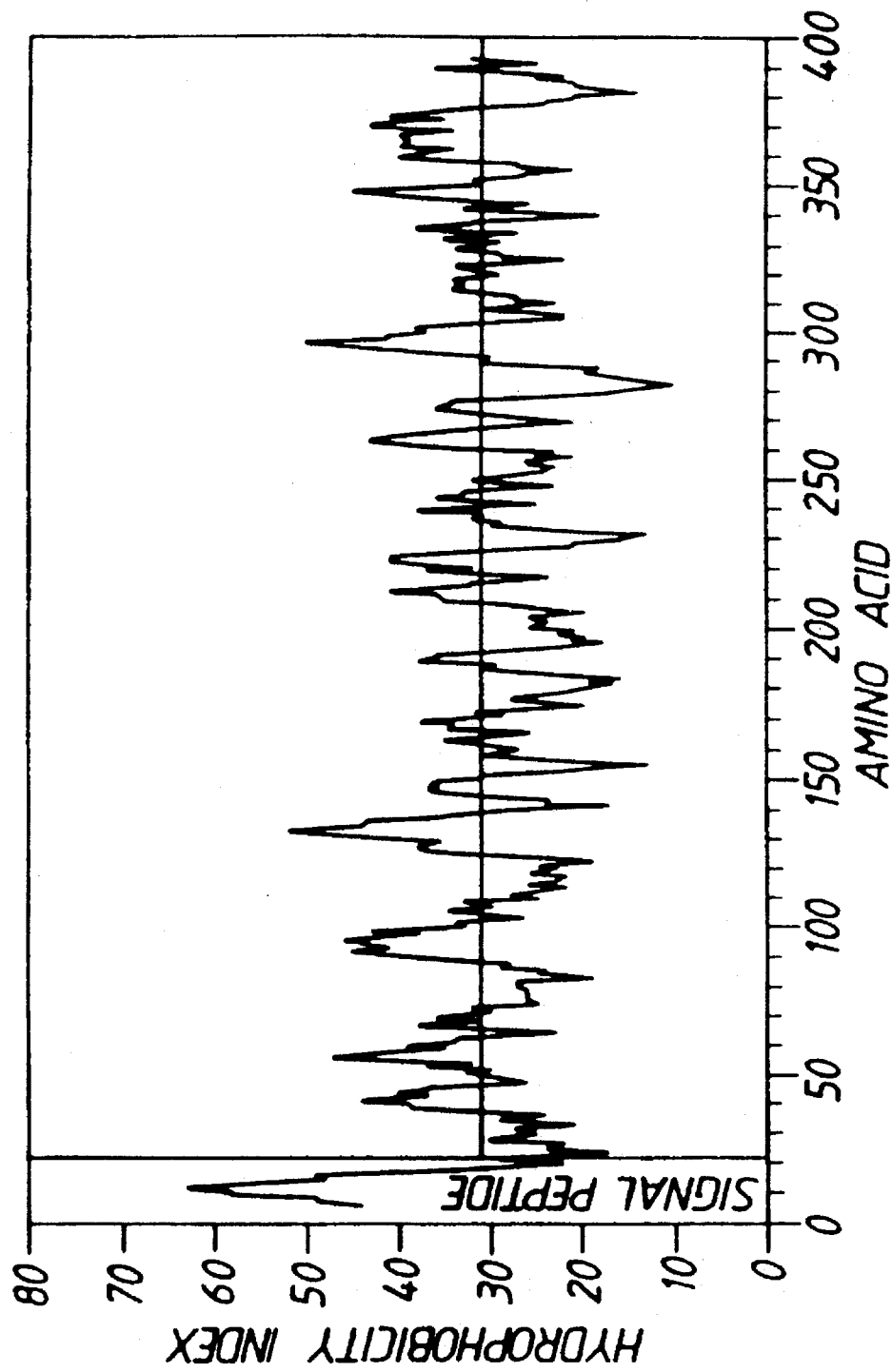

FIG. 4 shows the hydrophobicity profile of the RAP-2 protein.

DETAILED DESCRIPTION OF THE INVENTION

There is considerable confusion in the literature as to the identity of the *P.falciparum* RAP-1 and RAP-2 proteins and to their relationship. Part of this appears to be due to the number of proteins reported to be in the rhoptries which have a size of approximately 80 kDa or 42 kDa; the propensity of some malarial proteins to be extracted as a series of proteolytically cleaved fragments and the coincidence that RAP-1 is approximately twice the size of RAP-2, prompting Perrin & Dayal (1982) to suggest that RAP-1 may be a dimer of RAP-2.

The RAP-1 protein is almost always isolated as a series of related bands which have apparently been produced by proteolysis of the parent molecule (Perrin et al., 1985, Schofield et al., 1986, Clark et al., 1987, Bushell et al., 1988, Ridley et al., 1990a). Several authors have suggested that RAP-2 may also be a cleavage product of RAP-1. For example, Ridley et al., (1990a) found that purified RAP-1 decomposed to give rise to a protein of approximately the same size as RAP-2, reinforcing this view. Since the RAP-1 and RAP-2 proteins are closely associated in non-ionic detergent extracts of parasites, antibodies directed against RAP-1 or RAP-2 immunoprecipitate both proteins. However, antibodies only react with RAP-1 or RAP-2 by Western Blotting (Bushell et al., 1988) or immunoprecipitate only RAP-1 or RAP-2 from SDS dissociated proteins (Clark et al., 1987), showing that the two are antigenically distinct. Bushell et al., (1988) presented data from peptide mapping to show that RAP-1 and its proteolytic cleavage products were unrelated to RAP-2.

This conclusion is confirmed by the data presented herein which show that RAP-1 and RAP-2 are different proteins coded by separate genes. Comparison of the sequences show that these proteins are quite different: no significant homology exists between the DNA or protein sequences. RAP-2 is considerably more basic than RAP-1. However, both have a number of moderately hydrophobic domains which probably accounts for the difficulty in keeping purified RAP-1, RAP-2 and their complex, QF3, in solution in the absence of detergents such as SDS (data not shown) and for the association of QF3 with membranous material apparently discharged from rhoptries (Bushell et al., 1988). No significant homology was found between the RAP-2 protein and any protein sequence in the NBRF data bank, or by comparing the RAP-2 protein sequence with the nucleic acid sequences in the GENBANK data base, translated in all 6 reading frames.

The RAP-2 used herein was derived from the QF3 complex. This was itself purified by immunoaffinity chromatography on monoclonal antibody 7H8/50 directed against RAP-1. An amino acid sequence determined from a V8 protease fragment of the RAP-1 protein isolated during this procedure is contained within the RAP-1 sequence determined by Ridley et al., (1990a). This conclusively demonstrates that the RAP-2 protein described in this paper and the RAP-1 protein described by Ridley et al., (1990a) are the two components of the QF3 complex. This is important since several other proteins with sizes approximating RAP-1 and RAP-2 have been described in the rhoptries.

Braun-Breton et al., (1988) reported a membrane-associated, phospholipase C activated serine protease from merozoites. This protein was synthesized as an 83 kDa protein which was processed to a 76 kDa mature protein and was reported (Braun-Breton et.al., quoted in Braun-Breton et al., 1988) as being anchored via a glycosylphosphatidylinositol (GPI) moiety. A monoclonal antibody, 31 c13 immunoprecipitates this protein and a smaller 41 kDa protein. This monoclonal antibody also gives the punctate immunofluorescence pattern characteristic of rhoptries (Dayal et al., 1986). In this earlier study, 31 c13 was reported to precipitate proteins of 82 kDa, 69 kDa, a doublet at 41 kDa with several other proteins of lower abundance. This published immunoprecipitation pattern is indistinguishable from that reported for QF3. However, neither RAP-1 nor RAP-2 have any homology with serine proteases and neither have the hydrophobic C terminal domain characteristic of other malarial and trypanosomal proteins anchored through a GPI moiety (Smythe et al., 1988). These data suggest that RAP-1 and the 76 kDa protease are not the same protein. There is a possibility that the 41 kDa doublet immunoprecipitated with the protease by 31 c13 could be RAP-2. While RAP-2 is clearly associated with RAP-1 in the QF3 complex, the data do not rule out the possibility that it may associate with other proteins. However, an alternative explanation is more likely. In addition to binding this membrane protease, 31 c13 has been reported as binding to the *P.falciparum* aldolase (Certa et al., 1988) which also has a size of 41 kDa.

On the basis of the immunofluorescence patterns obtained for a series of monoclonal antibodies directed against the

*P.falciparum* aldolase Perrin et al., (1985) and Certa et al., (1988) suggest that the aldolase is also in the rhoptries leading to the deduction that RAP-2 is the aldolase. The rhoptry location is surprising since aldolase is normally found in the cytoplasm of cells. Unlike other rhoptry proteins, the aldolase has no signal peptide so it is not clear how it would be incorporated into the rhoptries. This reported rhoptry location is in contrast to the report by Knapp et al. (1990) who report the aldolase present in the parasite cytoplasm.

The sequence data obtained herein clearly show that RAP-2 is not aldolase. Although the parasite aldolase shows no significant homology to RAP-2, the possibility still remains that they may share, by chance, a common epitope. Cross reactivity has been frequently observed with other malarial proteins (Saul et al., 1989) and there are several tripeptides shared by both sequences which could form the basks of shared epitopes.

The identity of the RAP-2 protein is important in interpreting the published vaccine studies in Saimiri monkeys. Perrin et al., (1985) used a mixture of proteins purified on monoclonal antibodies 28 c11 directed against aldolase, 31 c13 directed against both the 82 kDa protease and aldolase and 50 c11 which immunoprecipitates an 82/41 kDa doublet located in the rhoptries which may be QF3. One group of monkeys received the mixture of all the proteins recognized by these monoclonal antibodies. A second group received a mixture of just the 41 kDa proteins. Both groups of monkeys showed significant protection but the group receiving the total mixture had lower peak parasitaemias. A major component in the 41 kDa mixture was aldolase. Although monoclonal antibody 28 c12 inhibited parasite growth in vitro (Perrin et al., 1981), in subsequent experiments, recombinant aldolase was ineffective in inducing protective immunity in Saimiri monkeys (Herrera et al., 1990). Therefore it is likely that RAP-2 was the effective component of the 41 kDa mixture.

Ridley et al., (1990b) vaccinated monkeys with a mixture of RAP-1 and RAP-2. These monkeys showed significant protection when challenged. The pre-challenge sera from these monkeys Western blotted both RAP-1 and RAP-2 showing that both proteins were immunogenic. Ridley et al., (1990a) believed that RAP-2 was a proteolytic breakdown product of RAP-1 and therefore interpreted their data as evidence for the protective effect of RAP-1. In view of the data presented herein, this needs to be re-evaluated.

The cloning of RAP-1 by Ridley et al., (1990a), and the present work on the cloning and expression of recombinant RAP-2 establishes the sequence of two of the major rhoptry proteins. They also provide the basis for preparing material to conclusively examine the role that these proteins may play in inducing protective immunity against *P.falciparum* in man. The lack of antigenic diversity found by MAbs, as reflected in the lack of sequence polymorphism in the gene coding for RAP-2, suggests that one of the major difficulties facing other malaria vaccine candidates may not be important for this protein.

Further features of the present invention, in particular the cloning and expression of the gene encoding the 42 kDa rhoptry-associated protein (RAP-2), are described in the following Example and in the accompanying drawings. Whilst one specific example of the cloning of the RAP-2 gene and of expression of recombinant RAP-2 is described in this Example, it will be understood by persons skilled in this art that once the structure of the RAP-2 gene is known from the disclosure herein, the cloning and expression of this gene may be performed by many different techniques using different vectors and host cells which are well known in the art. Accordingly, it will be understood that the present invention is not restricted to the particular techniques, vectors, host cells and the like which are described herein by way of example only.

Figure 1:
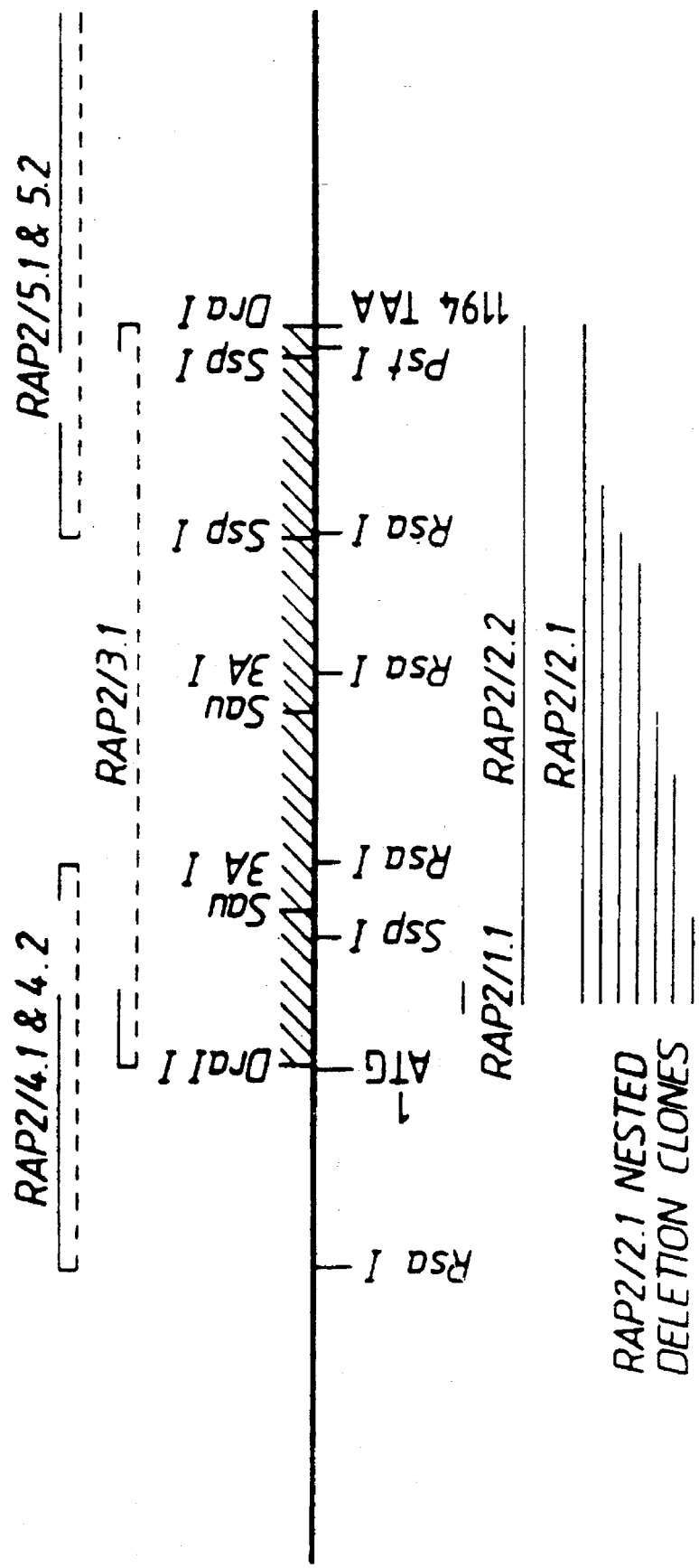
FIG. 1 shows the restriction map and cloning strategy of the RAP-2 gene. Restriction sites shown are those confirmed experimentally. Bars represent the area encoded in each clone with thick line indicating the region sequenced. RAP-2/3, 4, 5 were generated from inverted PCR and the clones contain discontinuous regions. The splice site in these clones is indicated by the dotted line.

FIG. 1 shows the restriction map and cloning strategy of the RAP-2 gene. Restriction sites shown are those confirmed experimentally. Bars represent the area encoded in each clone with thick line indicating the region sequenced. RAP-2/3,4,5 were generated from inverted PCR and the clones contain discontinuous regions. The splice site in these clones is indicated by the dotted line.

Figure 2A:
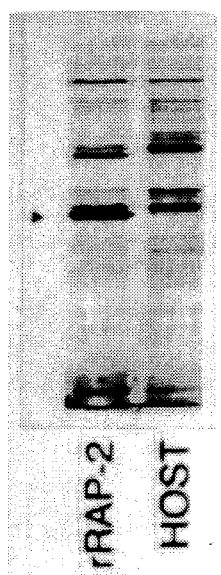
FIGS. 2A and 2B show expression of recombinant RAP-2. Transformed bacterial cells were grown in tryptone soya broth to an $A_{550}$ of 9.8 to 1.0 and induced with 2 mM β-isopropylthiogalactoside as described by Stüber et al., (1990). After boiling in the presence of 5% β-mercaptoethanol, SDS solubilized protein from extracts of D10 schizonts of from induced bacterial cells transfected with the RAP-2 recombinant or expression plasmid alone were separated by SDS PAGE on 12% polyacrylamide gels.
Figure 2B:
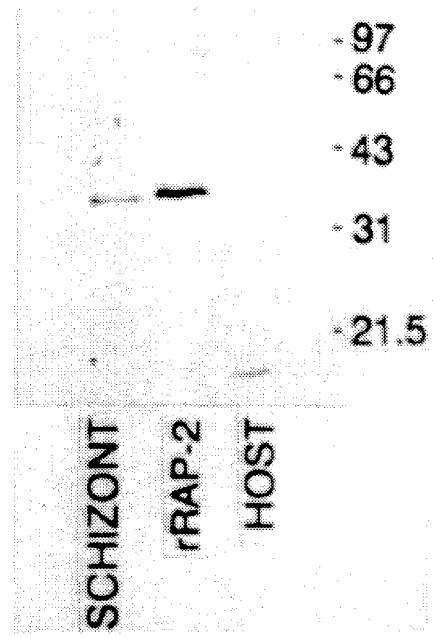

FIG. 2 shows expression of recombinant RAP-2. Transformed bacterial cells were grown in tryptone soya broth to an $A_{550}$ of 9.8 to 1.0 and induced with 2 mM β-isopropylthiogalactoside as described by Stüber et.al., (1990). After boiling in the presence of 5% β-mercaptoethanol, SDS solubilized protein from extracts of D10 schizonts or from induced bacterial cells transfected with the RAP-2 recombinant or expression plasmid alone were separated by SDS PAGE on 12% polyacrylamide gels. Gels were either (A) stained with Coomassie blue or (B) transferred to nitrocellulose and probed with MAb 3A9/48 as previously described (Bushell et.al., 1988). Position of the RAP-2 is indicated: on this 12% gel system, RAP-2 has an apparent size of 35 kDa, previous estimates of approximately 40 kDa were based on 7.5% polyacrylamide gels.

FIG. 3 shows:

(A) the nucleotide and deduced amino acid sequence of the RAP-2 clone (SEQ ID NO:19).

(B) the polymorphism detected in the RAP-2 sequences of the D10, 3D7, HB3 and Palo Alto lines in the nucleotide and translated amino acid sequences (SEQ ID NOS:20–23).

FIG. 4 shows the hydrophobicity profile of the RAP-2 protein.

EXAMPLE

EXPERIMENTAL PROCEDURES

Parasite Cultures

*P.falciparum* lines were grown in vitro in human red cells and 10% serum (Trager and Jensen, 1975). The following lines were used for immunofluorescence studies: D10 clone of FCQ-27/PNG (Anders et al., 1983); clone 3D7 of NF54, clone HB3 of H1, clone XCL10 from a cross of 3D7 and HB3 (Walliker et al., 1987); Palo Alto (Chang et al., 1988), Malayan Camp (Leech et al., 1984); Indochina 1 and FVO (Stanley et al., 1985); clone ITG2 (Mattei et al., 1988); FCR3 (Hadley et al., 1983); Wellcome-Liverpool (Holder & Freeman, 1982); clone 7G8 (Burkot et al., 1984), K1 (Thaitong & Beale, 1981), V1 (Stahl et al., 1985), clone T9/94 (Thaitong et al., 1984). DNA from D10, 3D7, HB3 and Palo Alto were used for sequencing the RAP-2 gene.

Monoclonal Antibodies and Immunofluorescence Assays

The 5 Mabs used in this study were 3A9/48, 3D9/50, 7H8/50, 3E6/64, 3H7/64, with isotypes $IgG_1$, $IgG_3$, $IgG_{2a}$, $IgG_{2a}$ and $IgG_{2a}$, respectively. 3E4/64 and 3H7/64 were obtained from mice immunized with affinity purified QF3 crosslinked to bovine serum albumin with glutaraldehyde, the other MAbs were from mice immunized with glutaraldehyde fixed schizonts of the FCQ-27/PNG isolate. On immunoblots of nonreduced parasites, 3A9/48, 3D9/50, 3E6/64 and 3H7/64 recognize RAP-2. 3A9/48 and 3D9/50 recognized the antigen on reduced blots. 7H8/50 recognizes RAP-1. Immunofluorescence assays were done on thin films of parasites, fixed for 10 min in acetone/methanol (90:10 v/v) at −20° C. as previously described (Bushell et al., 1988).

Protein Purification and N Terminal Sequencing

QF3 was purified by immunoaffinity chromatography using 7H8/50 and preparative electrophoresis then cleaved with *Staphylococcus aureus* V8 protease as previously described (Bushell et al., 1989). Intact QF3 complex or the individual V8 cleaved peptides were electrophoresed using the discontinuous SDS polyacrylamide system of Moos et al., (1988). Following electrophoresis, the proteins were electrophoretically transferred to a polyvinyl difluoride membrane, stained with 0.1% coomassie blue R250 in 50% methanol for 5 min, destained for 10 min in 50% methanol and washed with water. The stained bands were excised then sequenced in an Applied Biosystems model 470 sequencer.

Cloning and DNA Sequencing

The polymerase chain reaction used to amplify RAP-2 gene fragments used the Perkin Elmer Cetus Gene Amp kit according to the manufacturers instructions. Forward primer [PR1F: cgaattcAAATT(A/G)TA(T/C)CCNGA, (SEQ ID NO:1) (lower case indicates added restriction sites)] and reverse primer [PR1R:gcaagctt(A/T)GC(A/T)GT(A/G)T-GNGC(A/G)TA] (SEQ ID NO:2) were synthesised using a model 381 oligonucleotide synthesiser (Applied Biosystems) and used to amplify a 69 bp fragment (54 bp of malaria sequence and 15 bp of linker). Following the first amplification, the DNA was electrophoresed on a 4% NuSieve agarose (FMC BioProducts, Me., U.S.A.), and the band corresponding to the expected size was excised, reamplified and cloned into M13mpl8. It was sequenced using the dideoxy chain termination method with [$^{35}$S]dATP and Klenow polymerase using standard techniques. This clone was used to probe Southern blots of digested DNA to produce a restriction map. On this map, the cloned sequence was contained within a 1.2 kb Dra I fragment. The sequence from the RAP2/1.1 clone to the 3' end of this Dra I fragment was amplified by ligating annealed double strand synthetic oligomer GTAAAACGACGGCCAGT (SEQ ID NO:3) (the M13 universal primer sequence) to Dra I restricted D10 DNA; size fractionating the ligated DNA on 1% agarose gel to remove excess oligomer, then amplifying this DNA in a PCR with M13 sequencing primer and a primer derived from the unique sequence in RAP-2/1.1, PR2F: gggaat-tcAAATTCTTTGACTGGTT. (SEQ ID NO:4) Initial attempts to clone Eco RI digested DNA into EcoR1/SmaI digested M13mpl8 and M13mpl9 DNA failed but were successful following digestion of the amplified DNA with Hae III which cuts within the M13 sequencing primer, to give clones in M13mpl8 (RAP2/2.1) and M13mpl9 (RAP2.2/2). A set of nested deletions were prepared using the Exonuclease III method of Henikoff (1984). Replicative form RAP2/2.1 was prepared and digested with Bam HI and Pst I. A Pst I site occurs within the RAP-2 sequence, however sufficient DNA remained intact to enable a set of deletion clones to be prepared. These clones were sequenced using taq polymerase and ABI 370 DNA Sequencer (Applied Biosystems) using the manufacturer's protocol. The 5' end of the Dra I fragment was cloned into M13mpl8 and sequenced following amplification in an inverted PCR (Triglia et al., 1989) using DNA cut with Dra I, ligated, then cut with Ssp I; (SEQ ID NO:5) and primers PR3R: gggaat-tcAACATGTGCAGTGTG and PR3F: gggaattcCA-GAAAACTTCAAAGC (SEQ ID NO:6) from the 5' and 3' regions of RAP2/2.1 respectively. Both the 5' and 3' ends and flanking regions of the RAP-2 gene were cloned and sequenced in further inverted PCR reactions. DNA was digested with Rsa I and religated. For the 5' sequence, this DNA was digested with Sau 3A then amplified using primer PR3R above and PR5F: gggaattCATGTTTTTGCTAGAG-CAG (SEQ ID NO:7). For the 3' sequence, the DNA was digested with Ssp I and amplified with primer PR3F above and PR6R: gggaattCGTGATTTTCATACATACC. (SEQ ID NO:8) Both amplified DNA fragments were digested with Eco RI, cloned into M13mpl8 and sequenced.

Chromosome Location

Southern blots of chromosomes were prepared as previously described (Limbaiboon et al., 1991). Briefly, agarose embedded blocks of D10, 3D7 and HB3 were prepared, lysed, and the chromosomes separated by pulse field gradient gel electrophoresis in 1% agarose with a pulse time of 150–270 sec (ramping) at 100 V for 24 h, 270 secs at 100 V for 20 h and finally 999 sec at 60 v for 52 h. The DNA was transferred to Hybond-N membranes (Amersham) then probed with labelled insert from RAP2/2.1. Chromosomes are numbered according the decreasing mobility of the 3D7 clone and the identity of chromosomes in other isolates confirmed with a panel of chromosome specific probes. Chromosome 5 on which the RAP-2 gene was located, hybridized to a probe containing part of the MESA gene (Coppel et al., 1986).

Analysis of Sequence Diversity

DNA from D10, HB3, 3D7 and Palo Alto was amplified using primers catcacggatccAAAAAAGAGCAA-CAAAATGGG (SEQ ID NO:9) and ctctagagtcgacTTAAA-GAACAATTAATTCTC (SEQ ID NO:10) corresponding to the N and C termini of the full length protein. The DNA was cut with Bam HI and Sal I and cloned into Bam HI/Sal I cut M13mpl8 and M13mpl9. Several clones from each parasite line were sequenced to give the 5' and 3' ends of the corresponding genes. The amplified DNA was digested with Rsa I and cloned into M13mpl8. Several clones covering both orientations from each isolate were sequenced.

Expression of the Recombinant protein

DNA from D10 and 3D7 was amplified using primers catcacggatccGATAAGTGTGAAACTG (SEQ ID NO:11) corresponding to the N terminus of the mature protein and the C terminal primer used above. Appropriately digested PCR amplification products were ligated into the Bam HI/Sal I site of the hexaHis expression vector pDS56/RBSII, 6XHIS (Stüber et.al., 1990) and the resulting recombinants were subsequently transformed into *E.coli* SG13009 (Gottesmann et.al., 1981). The host strain had been transformed previously with the lacI-bearing plasmid, pUHA1. The transformed bacterial cells were grown as described previously and the recombinant protein was expressed as an insoluble inclusion body. It was substantially purified (>80% pure) by dissolving the cells in 6M guanidine hydrochloride, 0.1M sodium phosphate, pH 8.0, followed by affinity chromatography on a nickel chelate column (Stüber et.al., 1990). The recombinant protein eluted in a pH 4.5 buffer containing 6M guanidine hydrochloride, or a pH 4.9 buffer containing 8M urea. A higher purity could be obtained by first purifying the inclusion bodies, as follows. Bacterial cells were resuspended in 24% sucrose, a 0.75M guanidine hydrochloride, 0.1M sodium phosphate, pH 7.5, and homogenised at 7000 psi with 6 passes through a Martin-Gaulin press. The homogenate was then centrifuged at 10,000 g for 15 minutes, and the pellet resuspended in 6M guanidine hydrochloride, 0.1M sodium phosphate, pH 7.0, and chromatographed as described above.

RESULTS

A.

**Protein Sequences of the RAP-1 and RAP-2 Proteins of *P.falciparum***

QF3 proteins isolated by immunoaffinity chromatography on monoclonal antibody 7H8/50 then subsequently separated by preparative SDS/PAGE were subjected to N terminal amino acid sequencing. RAP-1 and its major breakdown products failed to give any N terminal sequence. RAP-2 returned the sequence D/TKXETE/A (SEQ ID NO:12) but with poor yield. Extensive sequences were obtained by analyzing *Staphylococcus aureus* V8 protease fragments derived from both RAP-1 and RAP-2. The 40 kDa V8 fragment of RAP-2 gave the sequence FSKLYPESNSLT-GLIYAHTA. (SEQ ID NO:13) A 48 kDa fragment of RAP-1 returned the sequence XMLYNXPNNSNLFD. (SEQ ID NO:14) This corresponds to positions 348–361 of the predicted amino acid sequence of RAP-1. This confirms that the 80 kDa protean recognised by 7H8/50 is RAP-1, and therefore the 42 kDa protein discussed herein is part of the same complex studied by Ridley et.al. (1990a).

Cloning of the RAP-2 Gene

PCR primers corresponding to the amino acid sequences KLYPE (SEQ ID NO:15) and YAHTA (SEQ ID NO:16) were constructed and used to amplify a 54 base pair length of DNA extracted from the *P.falciparum* parasite line D10. The fragment was cloned (clone RAP2/1.1 in FIG. 1) and sequenced. The intervening DNA between the primer sequence coded for the expected amino acid sequence SNSLTGLI (SEQ ID NO:17). Southern blotting indicated that this sequence was contained within a 1.2 kb Dra1 fragment. A synthetic, double stranded oligonucleotide corresponding to the M13 universal sequencing primer was ligated to 1–2 kb size selected, Dra1 cut D10 DNA. This was used as a template in the PCR reaction using primer derived from the 54 base pair original PCR amplified fragment and the M13 sequencing primer to amplify a 1 kb fragment of DNA. This was cloned into Eco RI/Sma I digested M13 mp18 (RAP-2/2.1) and M13 mp19 (RAP-2/2.2) then sequenced. As shown in FIG. 1, RAP-2/2.1 was sequenced through the use of a series of ordered deletion mutants generated using exonuclease III (Henikoff, 1984). The sequence of the 5' end of this Dra1 fragment was completed using an inverted PCR (Triglia et.al., 1988). This Dra1 fragment had a single open reading frame but did not contain an initial ATG codon characteristic of a start codon. The 3' end of the clone ended with a TAA codon which formed part of the Dra1 cleavage site. The sequences of the flanking regions were obtained through the use of further inverted PCR reactions using Rsa1 cut DNA (FIG. 1).

DNA from the D10 and 3D7 clones of *P.falciparum* was amplified in a PCR and cloned into the hexaHis vector pDS56/RBS11 to give a construct theoretically coding for the entire mature form of RAP-2. *E. coli* transfected with this construct expressed a 42 kDa protein when induced with IPTG. This recombinant protein has a similar size to the native protein and reacted by immunoblotting with MAb 3D9/50 directed against RAP-2, providing further evidence that the cloned gene codes for RAP-2 (FIG. 2).

Structure of the RAP-2 Gene

The sequence of the RAP-2 gene from the D10 clone is shown in FIG. 3. The initial ATG is preceded by an AT rich region terminating in a sequence close to the transcription initiation consensus sequence observed in other malarial genes (Saul and Battistutta, 1990). The coding region had a codon usage and a base bias similar to that of other malarial coding regions (Saul and Battistutta, 1988).

The RAP-2 gene was localised to chromosome 5 in the D10, 3D7 and HB3 clones on Southern blots of chromosomes separated by pulse-field gradient electrophoresis. It is located in a region with few 6 base restriction sites. Restriction fragments obtained with Bam HI, Hind III, Pst I, Kpn I, Eco RI, Eco RV and Sal I were too large to be resolved on a 1% agarose gel. A restriction map was prepared using Dra I, Ssp I, Pst I, Sau 3a I and Rsa I alone and in combination. This was consistent with the position of the restriction sites determined by sequencing the cloned genes (FIG. 1).

Structure of the RAP-2 Protein

The cloned sequence codes for a protein of 398 amino acids. The protein commences with a sequence with the characteristics of a signal peptide. The SIGSEQ1 program of Folz et.al. (1986) predicts a cleavage occurring between glycine 21 and aspartic acid 22 resulting in a mature protein with an N terminal sequence of DKCETE. (SEQ ID NO:18) This sequence closely matches the sequence (D/TKXETA/E) (SEQ ID NO:12) obtained in low abundance from the isolated native protein. We conclude that the mature protein contains 377 amino acids, with a calculated size of 44,487 Da. This is in good agreement with the observed size of 42 kDa by SDS polyacrylamide gel electrophoresis. Unlike many malarial proteins, the mature protein lacks repetitive elements and contains markedly hydrophobic domains (FIG. 4). (Kyte and Doolittle, 1982) although none of these has the characteristics of a membrane spanning domain (Klein et.al., 1985). The protein is quite basic with a calculated pI of 8.9. Using the sequence data of Ridley et.al., (1990a) for RAP-1, we calculate that the pI of RAP-1 is 6.9 and that of the QF3 complex is 8.2. This is in agreement with the observed pI for this complex (Crewther et.al., 1990).

The mature protein contains 4 cysteines. At least 2 of these are disulfide bonded since there is a substantial shift in the electrophoretic mobility of RAP-2 in SDS gels following treatment with reducing agents (Bushell et.al., 1988).

Sequence Diversity in RAP-2

DNA corresponding to the RAP-2 gene from *P.falciparum* clones D10, 3D7, HB3 and the monkey adapted isolate Palo Alto was amplified using a PCR reaction with primers corresponding to the first 6 amino acids of the signal sequence and the C terminal 5 amino acids. Sequences of each of these fragments indicated that the RAP-2 gene shows little sequence variation between isolates (FIG. 3). The nucleotide sequences of HB3 and Palo Alto were identical. There were two base changes between HB3 and 3D7, changing a CTT codon to TTA but as both these code for leucine the predicted amino acid sequences of Palo Alto, 3D7 and HB3 are identical. The D10 sequence is different, with the 3 base changes between the HB3 sequence and that of D10 all giving amino acid substitutions.

This lack of diversity is in keeping with the lack of antigenic diversity detected with MAbs directed against RAP-2. All 4 MAbs reacted with all 16 parasite lines tested. In spite of this conservation between isolates of *P.falciparum*, when Southern blots of the DNA from the rodent malaria species, *P. chabaudi*, *P. yoelii*, *P. berghei*, and *P. vinkei* were probed with the 1 kb RAP2/2.1 clone, no hybridizing band could be found even at modest stringency.

REFERENCES

Anders, R. F., Brown, G. V. and Edward, A. (1983). *Proc. Natl. Acad. Sci. (USA).* 80:529–539.

Braun-Breton, C., Rosenberry, T. L. and Pereira da Silva, L. (1988). *Nature* 322:487–459.

Burkot, T. R., Williams, J. L. and Schneider, I. (1984). *Trans. Roy. Soc. Trop. Hyg.* 78:339–341.

Bushell, G. R., Ingram, L. T., Fardoulys, C. A. and Cooper, J. A. (1988). *Mol. Biochem. Parasitol.* 28:105–112.

Campbell, G. H., Miller, L. H., Hudson, D., Franco, E. L. and Andrysiak, P. M. (1984) *Am. J. Trop. Med. Hyg.* 33(6):1051–1054.

Certa, U., Ghersa, P., Dobeli, H., Matile, H., Kocker, H. P., Shrivastava, I. K., Shaw, A. R. and Perrin, L. H. (1988). *Science* 240:1035–1038.

Chang, S. P., Kramer, K. J., Yamaga, K. M., Kato, A., Case, S. E. and Siddiqui, W. A. (1988). *Exp. Parasitol.* 67:1–11.

Clark, J. T., Anand, R., Akoglu, T. and McBride, J. S. (1987). *Parasitol. Res.* 73:425–434.

Cooper, J. A., Ingram, L. T., Bushell, G. R., Fardoulys, C. A., Stenzel, D., Schofield, L. and Saul, A. J. (1988). *Mol. Biochem. Parasitol.* 29:251–260.

Coppel, R. L., Culvenor, G., Bianco, A. E., Crewther, P. E., Stahl, H. D., Brown, G. V., Anders, R. F. and Kemp, D. J. (1986). *Mol. Biochem. Parasitol.* 20:265–277.

Crewther, P. E., Culvenor, J. G., Silva, A., Cooper, J. A. and Anders, R. F. (1990). *Exp. Parasitol.* 70:193–206.

Folz, R. J. and Gordon, J. I. (1987). *Biochem. Biophys. Res. Comm.* 146:870–877.

Freeman, R. R., Trejdosiewics, A. J. and Cross, G. A. M. (1980). *Nature* 284:366–368.

Gottesmann, S., Halpern, E. and Trisler, P. (1981). *J. Bacteriol.* 148:165–273.

Hadley, T. J., Klotz, F. W. and Miller, L. H. (1986). *Ann. Rev. Microbiol.* 40:451–477.

Hadley, T. J., Leech, J. H., Green, T. J., Daniel, W. A., Whalgren, M., Miller, L. H. and Howard, R. J. (1983). *Mol. Biochem. Parasitol.* 9:271–278.

Henikoff, S. (1984). *Gene* 28:351–359.

Herrera, S., Herrera, M. A., Perlaza, B. L., Burki, Y., Caspers, P., Dobeli, H., Rotmann, D. and Certa, U. (1990). *Proc. Natl. Acad. Sci. (USA)*. 87:4017–4021.

Holder, A. A. and Freeman, R. R. (1981). *Nature* 294:361–364.

Holder, A. A. and Freeman, R. R. (1982). *J. Exp. Med.* 156:1528–1538.

Holder, A. A., Freeman, R. R., Uni, S. and Aikawa, M. (1985). *Mol. Biochem. Parasitol.* 14:292–303.

Howard, R. F., Stanley, H. A., Campbell, G. H. and Reese, R. T. (1984). *Am. J. Trop. Med. Hyg.* 33(6):1055–1059.

Klein, P., Kanehisa, M. and DeLisi, C. (1985). *Biochim. Biophys. Acta.* 815:468–476.

Knapp, B., Hundt, E. and Kupper, H. A. (1990). *Mol. Biochem. Parasitol.* 40:1–12.

Kyte, J. and Doolittle, R. F. (1982). *J. Mol. Biol.* 157:105–132.

Leech, J. H., Barnwell, J. W., Miller, L. H. and Howard, R. J. (1984). *J. Cell Biol.* 98:1256–1264.

Limpaiboon, T., Shirley, M. W., Kemp, D. J. and Saul, A. (1991). *Mol. Biochem. Parasitol.* (in press).

Mattei, D., Langsley, G., Braun-Breton, C., Guillotte, M., Dubrementx, F-F and Mercereau-Puijlon, O. (1988). *Mol. Biochem. Parasitol.* 27:171–180.

Miller, L. H., Howard, R. J., Carter, R., Good, M. F., Nussenzweig, V. and Nussenzweig, R. S. (1986). *Science* 234:1349–1356.

Moos, M., Nguyen, Y. J. and Liu, T. Y. (1988). *J. Biol. Chem.* 263:6005–6008.

Perrin, L. H., Ramirez, E., Lambert, P. H. and Miescher, P. A. (1981). *Nature* 289:301–303.

Perrin, L. H. and Dayal, R. (1982). *Immunol. Rev.* 61:245–267.

Perrin, L. H., Merkil, B., Gabra, M. S., Stocker, J. W., Chizzolini, C. and Richie, R. (1985). *J. Clin. Invest.* 75:1718–1721.

Peterson, M. G., Marshall, V. M., Smythe, J. A., Crewther, P. E., Lew, A., Silva, A., Anders, R. F. and Kemp, D. J. (1989). *Mol. Cell. Biol.* 9:3151–3154.

Ridley, R. G., Takacs, B., Lahm, H., Delves, C. J., Goman, M., Certa, U., Matile, H., Woollett, G. R. and Scaife, J. G. (1990a). *Mol. Biochem. Parasitol.* 41:125–134.

Ridley, R. G., Takacs, B., Etlinger, H. and Scaife, J. G. (1990b). *Parasitol.* 101:187–192.

Roger, N., Dubremetz, J., Delplace, P., Foriter, B., Tronchin, G. and Vernes, A. (1988). *Mol. Biochem. Parasitol.* 27:135–142.

Saul, A. and Battistutta, D. (1988). *Mol. Biochem. Parasitol.* 27:35–42.

Saul, A. and Battistutta, D. (1990). *Mol. Biochem. Parasitol.* 42:55–62.

Saul, A., Lord, R., Jones, G., Geysen, H. M., Gale, J. and Mollard, R. (1989). *Parasite Immunol.* 11:593–601.

Schofield, L., Bushell, G. R., Cooper, J. A., Saul, A. J., Upcroft, J. A. and Kidson, C. (1986). *Mol. Biochem. Parasitol.* 18:183–195.

Siddiqui, W. A., Tam, L. Q., Kan, S., Kramer, K. J., Case, S. E., Palmer, K. L., Yamaga, K. M. and Hui, G. S. N. (1986). *Infect. Immun.* 51(1):314–318.

Smythe, J. A., Coppel, R. L., Brown, G. V., Ramasamy, R., Kemp, D. J. and Anders, R. F. (1988). *Proc. Natl. Acad. Sci. (USA)* 85:5195–5199.

Stahl, H. D., Kemp, D. J., Crewther, P. E., Scanlon, D. B., Woodrow, G., Brown, G. V., Bianco, A. E., Anders, R. F. and Coppel, R. L. (1985). *Nucl. Acids Res.* 13:7837–7846.

Stanley, H. A., Howard, R. F. and Reese, R. T. (1985). *J.Immunol.* 134:3439–3444.

Stüber, D., Matile, H. and Garotta, G. (1990). In Lefkowits, I. and Pernis, B. (eds). *Immunological Methods*, Academic Press, New York, Vol. IV, pp.121–152.

Thaitong, S. and Beale, G. H. (1981). *Trans. Roy. Soc. Trop. Med. Hyg.* 75:271–273.

Thaitong, S., Beale, G. H., Fenton, B., McBride, J., Rosario, V., Walker, A. and Walliker, D. (1984). *Trans. Roy. Soc. Trop. Med. Hyg.* 78:242–245.

Triglia, T., Peterson, M. G. and Kemp, D. J. (1988). *Nucl. Acids Res.* 16:8186.

Walliker, D., Quakyi, I. A., Wellems, T. E., McCutchen, T. F., Szarfman, A., London, W. T., Corcoran, L. M., Burkot, T. R. and Carter, R. (1987). *Science* 236:1661–1666.

---

We claim:

1. A recombinant DNA molecule comprising the nucleotide sequence of SEQ ID NO:19, or a fragment of said nucleotide sequence encoding an antigenic fragment of the *Plasmodium falciparum* 42 kDa rhoptry-associated protein (RAP-2).

2. The recombinant DNA molecule of claim 1 further comprising an expression control sequence operatively linked to a nucleotide sequence of claim 1.

3. A recombinant DNA cloning vector comprising a recombinant DNA molecule according to either claim 1 or 2.

4. A recombinant DNA cloning vector according to claim 3, wherein said vector is a plasmid.

5. A host cell comprising a recombinant DNA molecule according to either claim 1 or 2.

6. A host cell according to claim 5, wherein said host cell is *Escherichia coli*.

7. A host cell transfected or transformed with a recombinant DNA cloning vector according to either claim 3 or 4.

8. A host cell according to claim 7, wherein said host cell is *Escherichia coli*.

* * * * *

SEQUENCE LISTING (1) GENERAL INFORMATION:

(iii) NUMBER OF SEQUENCES: 23

( 2 ) INFORMATION FOR SEQ ID NO:1:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

CGAATTCAAA TTWTAYCCNG A                                            21

( 2 ) INFORMATION FOR SEQ ID NO:2:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

GCAAGCTTWG CWGTRTGNGC RTA                                     23

( 2 ) INFORMATION FOR SEQ ID NO:3:

( i ) SEQUENCE CHARACTERISTICS:
        ( A ) LENGTH: 17 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:3:

GTAAAACGAC GGCCAGT                                                    17

( 2 ) INFORMATION FOR SEQ ID NO:4:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

GGGAATTCAA ATTCTTTGAC TGGTT                                  25

( 2 ) INFORMATION FOR SEQ ID NO:5:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

GGGAATTCAA CATGTGCAGT GTG                                     23

( 2 ) INFORMATION FOR SEQ ID NO:6:

( i ) SEQUENCE CHARACTERISTICS:

( A ) LENGTH: 24 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:6:

GGGAATTCCA GAAAACTTCA AAGC 24

( 2 ) INFORMATION FOR SEQ ID NO:7:

( i ) SEQUENCE CHARACTERISTICS:
( A ) LENGTH: 25 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:7:

GGGAATTCAT GTTTTGCTAG AGCAG 25

( 2 ) INFORMATION FOR SEQ ID NO:8:

( i ) SEQUENCE CHARACTERISTICS:
( A ) LENGTH: 26 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:8:

GGGAATTCGT GATTTTCATA CATACC 26

( 2 ) INFORMATION FOR SEQ ID NO:9:

( i ) SEQUENCE CHARACTERISTICS:
( A ) LENGTH: 33 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:9:

CATCACGGAT CCAAAAAAGA GCAACAAAAT GGG 33

( 2 ) INFORMATION FOR SEQ ID NO:10:

( i ) SEQUENCE CHARACTERISTICS:
( A ) LENGTH: 33 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:10:

CTCTAGAGTC GACTTAAAGA ACAATTAATT CTC 33

( 2 ) INFORMATION FOR SEQ ID NO:11:

( i ) SEQUENCE CHARACTERISTICS:
( A ) LENGTH: 28 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:11:

CATCACGGAT CCGATAAGTG TGAAACTG 28

( 2 ) INFORMATION FOR SEQ ID NO:12:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:12:

Xaa Lys Xaa Glu Thr Xaa
1               5

( 2 ) INFORMATION FOR SEQ ID NO:13:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:13:

Phe Ser Lys Leu Tyr Pro Glu Ser Asn Ser Leu Thr Gly Leu Ile Tyr
1               5                   10                  15
Ala His Thr Ala
            20

( 2 ) INFORMATION FOR SEQ ID NO:14:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:14:

Xaa Met Leu Tyr Asn Xaa Pro Asn Asn Ser Asn Leu Phe Asp
1               5                   10

( 2 ) INFORMATION FOR SEQ ID NO:15:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:15:

Lys Leu Tyr Pro Glu
1               5

( 2 ) INFORMATION FOR SEQ ID NO:16:

( i ) SEQUENCE CHARACTERISTICS:
        ( A ) LENGTH: 5 amino acids
        ( B ) TYPE: amino acid
        ( C ) STRANDEDNESS: single (D) TOPOLOGY: linear (ii) MOLECULE TYPE: peptide (xi) SEQUENCE DESCRIPTION: SEQ ID NO:16:

Tyr Ala His Thr Ala
1               5

(2) INFORMATION FOR SEQ ID NO:17:

(i) SEQUENCE CHARACTERISTICS:
 (A) LENGTH: 8 amino acids
 (B) TYPE: amino acid
 (C) STRANDEDNESS: single
 (D) TOPOLOGY: linear (ii) MOLECULE TYPE: peptide (xi) SEQUENCE DESCRIPTION: SEQ ID NO:17:

Ser Asn Ser Leu Thr Gly Leu Ile
1               5

(2) INFORMATION FOR SEQ ID NO:18:

(i) SEQUENCE CHARACTERISTICS:
 (A) LENGTH: 6 amino acids
 (B) TYPE: amino acid
 (C) STRANDEDNESS: single
 (D) TOPOLOGY: linear (ii) MOLECULE TYPE: peptide (xi) SEQUENCE DESCRIPTION: SEQ ID NO:18:

Asp Lys Cys Glu Thr Glu
1               5

(2) INFORMATION FOR SEQ ID NO:19:

(i) SEQUENCE CHARACTERISTICS:
 (A) LENGTH: 1519 base pairs
 (B) TYPE: nucleic acid
 (C) STRANDEDNESS: double
 (D) TOPOLOGY: linear (ii) MOLECULE TYPE: DNA (genomic)

(ix) FEATURE:
 (A) NAME/KEY: CDS
 (B) LOCATION: 61..1254

(xi) SEQUENCE DESCRIPTION: SEQ ID NO:19:

```
TTTGTTTTTA TTTTAATAT AACATCATAC AGTTAAAAAA AAAAAAAAAA GAGCAACAAA           60

ATG GGT TTA AAA TTT TAT GTA TTA GTT TTT CTT ATT TTA TGT TTG AAG          108
Met Gly Leu Lys Phe Tyr Val Leu Val Phe Leu Ile Leu Cys Leu Lys
1               5                   10                  15

AAT GTT GTA AAA GGG GAT AAG TGT GAA ACT GAA TTT TCA AAA TTA TAT          156
Asn Val Val Lys Gly Asp Lys Cys Glu Thr Glu Phe Ser Lys Leu Tyr
            20                  25                  30

CCG GAA TCA AAT TCT TTG ACT GGT TTA ATT TAT GCA CAC ACT GCA CAT          204
Pro Glu Ser Asn Ser Leu Thr Gly Leu Ile Tyr Ala His Thr Ala His
        35                  40                  45

GTT CAT AAA TTA TCT ATG TGG GTT TAT TTT ATT TAT AAT CAC TTT AGT          252
Val His Lys Leu Ser Met Trp Val Tyr Phe Ile Tyr Asn His Phe Ser
    50                  55                  60

AGT GCA GAT GAA TTA ATA AAA TAT TTA GAA AAA ACC AAC ATA AAT ACT          300
Ser Ala Asp Glu Leu Ile Lys Tyr Leu Glu Lys Thr Asn Ile Asn Thr
65                  70                  75                  80
```

| | | | | | | | | | | | | | | | | |
|---|---|---|---|---|---|---|---|---|---|---|---|---|---|---|---|---|
| TTA | GAA | AAT | AGT | GAT | CAT | ACA | TGT | TTT | GCT | AGA | GCA | GTT | ACT | TTA | TAT | 348 |
| Leu | Glu | Asn | Ser | Asp | His | Thr | Cys | Phe | Ala | Arg | Ala | Val | Thr | Leu | Tyr | |
| | | | | 85 | | | | | 90 | | | | | 95 | | |
| TTG | TTT | TAT | TAC | TAT | CTT | AAG | GAT | ATT | AAG | TCT | ATG | TTA | AGT | ACA | GAT | 396 |
| Leu | Phe | Tyr | Tyr | Tyr | Leu | Lys | Asp | Ile | Lys | Ser | Met | Leu | Ser | Thr | Asp | |
| | | | 100 | | | | | 105 | | | | | 110 | | | |
| GAT | TAT | CAA | TCA | TTT | TTT | AAG | AAT | AAA | TTC | AAA | GAT | ATT | AAT | CCA | TTG | 444 |
| Asp | Tyr | Gln | Ser | Phe | Phe | Lys | Asn | Lys | Phe | Lys | Asp | Ile | Asn | Pro | Leu | |
| | | 115 | | | | | 120 | | | | | 125 | | | | |
| TTT | ATT | AAT | GAT | TTT | ATT | TTA | ATT | CTT | AAT | GAT | AAG | AAA | TTT | ATG | GAA | 492 |
| Phe | Ile | Asn | Asp | Phe | Ile | Leu | Ile | Leu | Asn | Asp | Lys | Lys | Phe | Met | Glu | |
| | 130 | | | | | 135 | | | | | 140 | | | | | |
| AAT | CTG | GAT | TTA | TAT | ATA | ATG | AAA | GAA | TCT | GAG | AGA | GAA | CAT | TTG | GTT | 540 |
| Asn | Leu | Asp | Leu | Tyr | Ile | Met | Lys | Glu | Ser | Glu | Arg | Glu | His | Leu | Val | |
| 145 | | | | | 150 | | | | | 155 | | | | | 160 | |
| ATA | AAG | AAG | AAT | CCA | TTT | TTA | CGT | GTA | TTG | AAT | AAA | GCA | TCA | ACT | ACT | 588 |
| Ile | Lys | Lys | Asn | Pro | Phe | Leu | Arg | Val | Leu | Asn | Lys | Ala | Ser | Thr | Thr | |
| | | | | 165 | | | | | 170 | | | | | 175 | | |
| ACA | CAT | GCA | ACA | TAT | AAG | TAT | AAT | CGA | TAC | TTT | ATA | GTA | GGA | TCA | AGA | 636 |
| Thr | His | Ala | Thr | Tyr | Lys | Tyr | Asn | Arg | Tyr | Phe | Ile | Val | Gly | Ser | Arg | |
| | | | 180 | | | | | 185 | | | | | 190 | | | |
| GTT | CAT | ACA | CCT | TAT | AAA | GAT | TAC | TTT | GGA | GAT | TTT | AAT | AAA | TAT | ACT | 684 |
| Val | His | Thr | Pro | Tyr | Lys | Asp | Tyr | Phe | Gly | Asp | Phe | Asn | Lys | Tyr | Thr | |
| | | 195 | | | | | 200 | | | | | 205 | | | | |
| GAG | ATA | AGT | GTA | CTT | AAT | TAT | GTT | CGT | GAT | TAC | AAT | TTT | TTA | ATT | TAT | 732 |
| Glu | Ile | Ser | Val | Leu | Asn | Tyr | Val | Arg | Asp | Tyr | Asn | Phe | Leu | Ile | Tyr | |
| | 210 | | | | | 215 | | | | | 220 | | | | | |
| GCT | GGT | TCA | AGG | GAA | AAT | TAC | TAC | AAT | TCA | GAT | ATA | GCT | GGA | CCA | GCA | 780 |
| Ala | Gly | Ser | Arg | Glu | Asn | Tyr | Tyr | Asn | Ser | Asp | Ile | Ala | Gly | Pro | Ala | |
| 225 | | | | | 230 | | | | | 235 | | | | | 240 | |
| AGA | AGT | GTT | AAT | AAT | GTA | ATT | AGT | AAG | AAT | AAA | ACA | TTA | GGA | TTG | AGA | 828 |
| Arg | Ser | Val | Asn | Asn | Val | Ile | Ser | Lys | Asn | Lys | Thr | Leu | Gly | Leu | Arg | |
| | | | | 245 | | | | | 250 | | | | | 255 | | |
| AAA | CGT | AGT | AGT | TCT | CTC | GCT | TTA | GTA | GGA | ACA | AAT | AAC | AAT | GAC | CCT | 876 |
| Lys | Arg | Ser | Ser | Ser | Leu | Ala | Leu | Val | Gly | Thr | Asn | Asn | Asn | Asp | Pro | |
| | | | 260 | | | | | 265 | | | | | 270 | | | |
| ATA | TTT | GCT | TAT | TGT | GAA | AAA | GAT | AAT | AAA | TCA | GAA | TAT | TAC | GGT | ACA | 924 |
| Ile | Phe | Ala | Tyr | Cys | Glu | Lys | Asp | Asn | Lys | Ser | Glu | Tyr | Tyr | Gly | Thr | |
| | | 275 | | | | | 280 | | | | | 285 | | | | |
| CCA | GAT | GAT | TTA | ATT | ACA | TCT | TTC | TTT | TCA | ATT | ATA | AAA | ACT | AAA | ATG | 972 |
| Pro | Asp | Asp | Leu | Ile | Thr | Ser | Phe | Phe | Ser | Ile | Ile | Lys | Thr | Lys | Met | |
| | 290 | | | | | 295 | | | | | 300 | | | | | |
| TTA | AAT | TCT | CAT | AAA | ACG | TTT | TTA | AGA | CAA | TTT | GAT | TAT | GCT | TTA | TTT | 1020 |
| Leu | Asn | Ser | His | Lys | Thr | Phe | Leu | Arg | Gln | Phe | Asp | Tyr | Ala | Leu | Phe | |
| 305 | | | | | 310 | | | | | 315 | | | | | 320 | |
| CAC | AAA | ACA | TAT | TCA | ATA | CCT | AAC | TTA | AAA | GGT | TTC | AGA | TTT | TTG | AAA | 1068 |
| His | Lys | Thr | Tyr | Ser | Ile | Pro | Asn | Leu | Lys | Gly | Phe | Arg | Phe | Leu | Lys | |
| | | | | 325 | | | | | 330 | | | | | 335 | | |
| CAC | CTT | TTC | CAA | AAA | AAG | AAT | TTA | GTG | AAT | TTT | GTA | GGT | ATG | TAT | GAA | 1116 |
| His | Leu | Phe | Gln | Lys | Lys | Asn | Leu | Val | Asn | Phe | Val | Gly | Met | Tyr | Glu | |
| | | | 340 | | | | | 345 | | | | | 350 | | | |
| AAT | CAC | GTA | TCA | ACA | GAA | ATA | AAT | TTC | TTA | GCT | GAA | GAT | TTC | GTT | GAA | 1164 |
| Asn | His | Val | Ser | Thr | Glu | Ile | Asn | Phe | Leu | Ala | Glu | Asp | Phe | Val | Glu | |
| | | 355 | | | | | 360 | | | | | 365 | | | | |
| TTA | TTT | GAT | GTA | ACT | ATG | GAT | TGT | TAT | TCT | CGC | CAA | TAT | TCA | AAC | CGT | 1212 |
| Leu | Phe | Asp | Val | Thr | Met | Asp | Cys | Tyr | Ser | Arg | Gln | Tyr | Ser | Asn | Arg | |
| | 370 | | | | | 375 | | | | | 380 | | | | | |
| GCT | GCA | GAA | AAC | TTC | AAA | GCT | ATT | AGA | GAA | TTA | AAT | GTT | CTT | | | 1254 |
| Ala | Ala | Glu | Asn | Phe | Lys | Ala | Ile | Arg | Glu | Leu | Asn | Val | Leu | | | |
| 385 | | | | | 390 | | | | | 395 | | | | | | |

|   |   |   |   |   |   |
|---|---|---|---|---|---|
| TAAAATAAAA | TACATTTATA | AATAAACATA | TAACTATTAC | AAAATACACA | TTTTTATATT | 1314 |
| TAAAGGTTTC | TCATAAATAT | GTTTTGTTT | GCTTTGTTT | TATTAATATT | ATTATTACTT | 1374 |
| TTTTGTTATT | TTATTTATT | TTAATTTTTT | TTTTTTTTG | TTTAAATAT | TTCTTTAAGT | 1434 |
| TGACATTTAA | ATATTATATT | ACAAGGAAAA | GGTCTTAAAT | ATATATATAT | ATATATGTAT | 1494 |
| ATATTTTCTT | TTAATGGGTA | AAAAG |   |   |   | 1519 |

( 2 ) INFORMATION FOR SEQ ID NO:20:

( i ) SEQUENCE CHARACTERISTICS:
        ( A ) LENGTH: 27 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 1..27

( x i ) SEQUENCE DESCRIPTION: SEQ ID NO:20:

GCACACACTG CAMATGTTCA TAAATTA      27

( 2 ) INFORMATION FOR SEQ ID NO:21:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:21:

Ala His Thr Ala Xaa Val His Lys Leu
1              5

( 2 ) INFORMATION FOR SEQ ID NO:22:

( i ) SEQUENCE CHARACTERISTICS:
        ( A ) LENGTH: 67 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 2..67

( x i ) SEQUENCE DESCRIPTION: SEQ ID NO:22:

TTATAAGTMT AATCCATACT TTATAGTAGG ATCAAGAGTT CATACACCTT ATAAAGATTA      60

CYTWGGA      67

( 2 ) INFORMATION FOR SEQ ID NO:23:

( i ) SEQUENCE CHARACTERISTICS:
        ( A ) LENGTH: 22 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:23:

Tyr Lys Xaa Asn Arg Tyr Phe Ile Val Gly Ser Arg Val His Thr Pro

|   |   |   |   |
|---|---|---|---|
| 1 | 5 | 10 | 15 |
| Tyr Lys Asp Tyr Xaa Gly | | | |
| 20 | | | |